United States Patent
Kim et al.

(10) Patent No.: US 7,966,074 B2
(45) Date of Patent: Jun. 21, 2011

(54) APPARATUS AND METHOD ENHANCING MUSCULAR MOVEMENT

(75) Inventors: Kyu-yong Kim, Yongin-si (KR);
Sang-youn Kim, Seoul (KR);
Byung-seok Soh, Suwon-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 0 days.

(21) Appl. No.: 11/797,760

(22) Filed: May 7, 2007

(65) Prior Publication Data

US 2007/0265140 A1 Nov. 15, 2007

(30) Foreign Application Priority Data

May 15, 2006 (KR) .................. 10-2006-0043516

(51) Int. Cl.
*A61N 1/00* (2006.01)
*A61B 5/04* (2006.01)

(52) U.S. Cl. .......... 607/49; 600/382; 600/388; 600/389; 600/390

(58) Field of Classification Search .................. 600/382, 600/388–390; 607/49
See application file for complete search history.

(56) References Cited

U.S. PATENT DOCUMENTS

| | | | |
|---|---|---|---|
| 4,408,600 A | | 10/1983 | Davis |
| 4,492,233 A | * | 1/1985 | Petrofsky et al. ............... 607/48 |
| 4,558,704 A | | 12/1985 | Petrofsky |
| 5,964,719 A | * | 10/1999 | Costello et al. ............... 600/595 |
| 6,781,284 B1 | * | 8/2004 | Pelrine et al. ............... 310/330 |
| 6,839,594 B2 | * | 1/2005 | Cohen et al. ............... 607/48 |
| 6,940,211 B2 | * | 9/2005 | Pelrine et al. ............... 310/330 |
| 7,365,647 B2 | * | 4/2008 | Nativ ............... 340/573.1 |
| 2002/0161415 A1 | * | 10/2002 | Cohen et al. ............... 607/48 |
| 2003/0212319 A1 | * | 11/2003 | Magill ............... 600/382 |
| 2004/0267331 A1 | * | 12/2004 | Koeneman et al. ............... 607/49 |
| 2005/0049652 A1 | * | 3/2005 | Tong ............... 607/48 |

FOREIGN PATENT DOCUMENTS

| | | |
|---|---|---|
| EP | 283387 A1 * | 9/1988 |
| FR | 2617701 A1 * | 1/1989 |
| FR | 2691350 A1 * | 11/1993 |
| JP | 9-241906 | 9/1997 |
| JP | 10-280209 | 10/1998 |
| JP | 2000-279536 | 10/2000 |
| KR | 10-0612031 | 8/2006 |

OTHER PUBLICATIONS

Korean Office Action for corresponding Korean Patent Application No. 10-2006-0043516 dated Sep. 19, 2007.
Korean Office Action for corresponding Korean Patent Application No. 10-2006-0043516 dated Mar. 26, 2007.

* cited by examiner

*Primary Examiner* — Niketa I Patel
*Assistant Examiner* — Nicole F Lavert
(74) *Attorney, Agent, or Firm* — Staas & Halsey LLP

(57) ABSTRACT

An apparatus to enhance muscular movement is provided. The apparatus includes at least one muscular movement sensor to sense a result of an attempt to move a muscle, a movement information controller to analyze the sensed muscular movement, and generate muscular movement information based on the analyzed muscular movements, and a muscular movement actuator to enhance the movement of the muscle according to the generated muscular movement information by actively controlling a deformation of the muscle movement actuator over the surface of the muscle.

14 Claims, 8 Drawing Sheets

APPARATUS AND METHOD ENHANCING MUSCULAR MOVEMENT

CROSS-REFERENCE TO RELATED APPLICATIONS

This application claims priority from Korean Patent No. 10-0772908 issued on Oct. 29, 2007 in the Korean Intellectual Property Office, the disclosure of which is incorporated herein by reference in its entirety.

BACKGROUND

1. Field

One or more embodiments of the present invention relate to an apparatus and method enhancing muscular movement, and more particularly, to an apparatus and method enhancing muscular movement using an electroactive polymer (EAP).

2. Description of the Related Art

In general, haptic feedback techniques are broadly classified into force feedback techniques and tactile feedback techniques. Force feedback techniques are techniques that enable a user to feel forces and a sense of movement using a mechanical interface. Force feedback devices are commonplace. Examples of force feedback devices include feedback force joysticks that apply repulsive forces to a game gun when the user shoots the gun while playing a game, and feedback force steering wheels to which virtual impulses are applied when a car crash occurs. The field of medicine is one of the fields of science in which tactile feedback has been most widely used. With tactile feedback, a doctor can conduct an operation on a virtual patient by referencing a 3D image that renders a three-dimensional anatomical structure, displayed in real time on a computer screen. Tactile feedback can be accomplished by stimulating mechanoreceptors of a user with a haptic device, or an array of small pins that is driven by compressed air or electricity, and can thus give a user the sensation that the user is actually touching skin.

Conventional apparatuses for encouraging muscular movement of a user are disclosed in U.S. Pat. No. 4,558,704 and Japanese Patent Laid-Open Gazette No. hei 10-280209.

In detail, U.S. Pat. No. 4,558,704 discloses a muscle stimulation system for patients with a paralyzed hand, particularly, a hand controller system that senses movement of the shoulder of a patient, having a paralyzed hand, with the aid of a sensor, provides the result of the sensing to a controller, and stimulates the patient's muscle under the control of the controller so that the patient can grab an object with the paralyzed hand. Japanese Patent Laid-Open Gazette No. hei 10-280209 discloses medical equipment for protection of the lower limbs. The medical equipment includes a power accumulation unit that reinforces the femoral muscle of a user. The medical equipment can prevent injury by assisting muscular contraction and encouraging muscle.

However, the aforementioned muscular movement encouraging apparatuses belong to a type of medical auxiliary equipment that can be worn by a user, and that can encourage muscular movement of the user. In order to use the aforementioned muscular movement encouraging apparatuses, a user must wear them with clothes on, and may accordingly feel heaviness on part of his/her body due to the weight of the necessary heavy components in each of the apparatuses.

SUMMARY

One or more embodiments of the present invention provide an apparatus and method enhancing muscular movement which is formed of fibers or pads as clothes that realize almost the same arrangement as that of the human muscles and can thus enhance the muscular movement of elderly people who have weak muscular strength.

Additional aspects and/or advantages of the invention will be set forth in part in the description which follows and, in part, will be apparent from the description, or may be learned by practice of the invention.

To achieve at least the above and/or other aspects and advantage, embodiments of the present invention include an apparatus to enhance a muscular movement. The apparatus includes at least one muscular movement sensor to sense a result of an attempt to move a muscle, a movement information controller to analyze the sensed muscular movement, and generate muscular movement information based on the analyzed muscular movements, and a muscular movement actuator to enhance the movement of the muscle according to the generated muscular movement information by actively controlling a deformation of the muscle movement actuator over the surface of the muscle.

To achieve at least the above and/or other aspects and advantage, embodiments of the present invention include a muscular movement actuator apparatus including an electroactive polymer (EAP) formed as clothing wearable over a surface of a muscle, a plurality of electrodes placed in contact with opposite lateral sides of the EAP, an electrical circuit to operatively connect to the electrodes, whereby a voltage applied to the electrical circuit causes a deformation of the EAP to enhance a movement of the muscle.

To achieve at least the above and/or other aspects and advantage, embodiments of the present invention include a method for enhancing a movement of a muscle including placing a surface of the muscle in contact with fibers comprised of an electroactive polymer (EAP), sensing the movement of the muscle using a plurality of sensors, analyzing the sensed muscular movement, generating muscular movement information based on the analyzed muscular movement, and enhancing the movement of the muscle, according to the generated muscular movement information using the EAP, by actively controlling a deformation of the EAP over the surface of the muscle.

BRIEF DESCRIPTION OF THE DRAWINGS

These and/or other aspects and advantages of the invention will become apparent and more readily appreciated from the following description of one or more embodiments, taken in conjunction with the accompanying drawings of which.

DETAILED DESCRIPTION OF EMBODIMENTS

Figure 1:
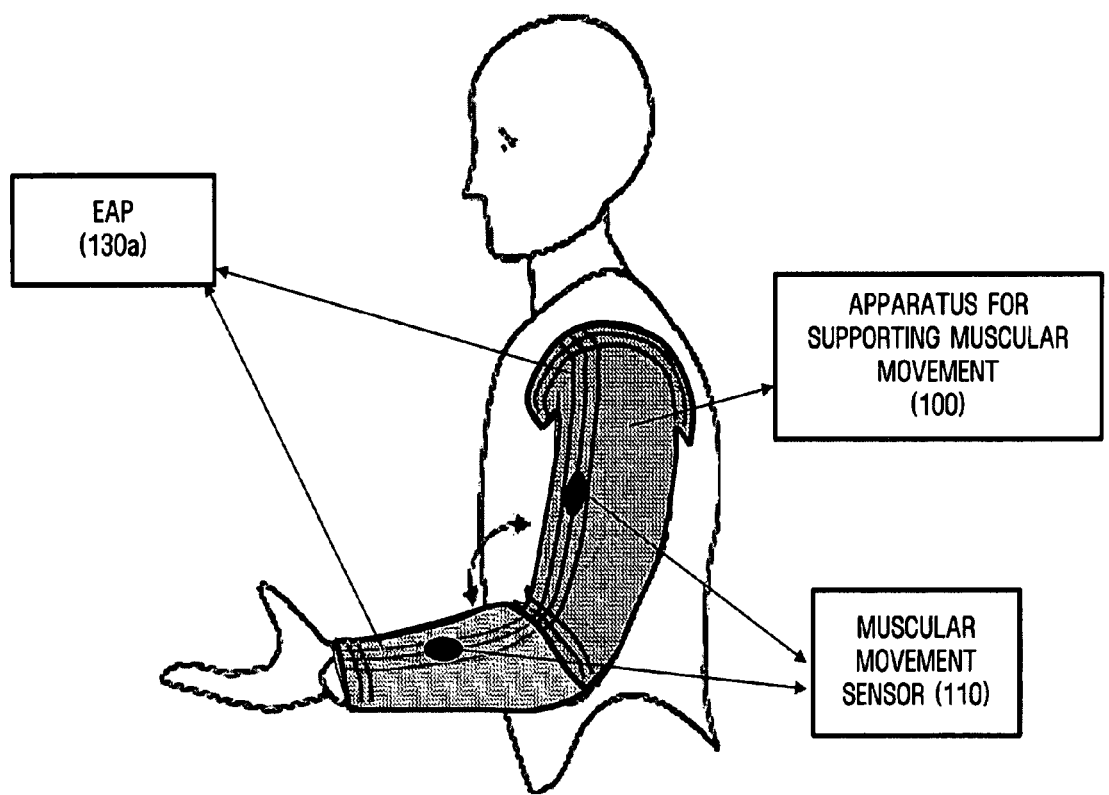
FIG. 1 illustrates a user who wears an apparatus for enhancing muscular movement according to an embodiment of the present invention.

Reference will now be made in detail to embodiments of the present invention, examples of which are illustrated in the accompanying drawings, wherein like reference numerals refer to the like elements throughout. Embodiments are described below to explain the present invention by referring to the figures.

FIG. 1 illustrates a user who wears an example apparatus 100 for enhancing muscular movement according to an embodiment of the present invention. Referring to FIG. 1, the apparatus 100 may be used as an auxiliary artificial muscle that is formed of fibers and can thus be worn by a user. For example, the apparatus 100 may be formed into clothing wearable by a user, such as a glove, stocking, wrap, or other wearable clothing.

In detail, in an embodiment a user may wear the apparatus 100 in order to supplement muscular strength. When a user who wears the apparatus 100 moves his/her left arm, as indicated by FIG. 1, a muscular movement sensor 110 of the apparatus 100 may sense the muscular movement of the user. Then, the result of the sensing may be analyzed, and an actuator, realized using an electroactive polymer (EAP) 130a, may be driven according to the result of the analysis, thereby enhancing the muscular movement of the user. Here, the user may feel as if he/she moved his/her muscle on his/her own without the auxiliary aid of the apparatus 100. The operation of the apparatus 100, according to an embodiment of the present invention, will hereinafter be described in further detail with reference to FIG. 2.

Figure 2:
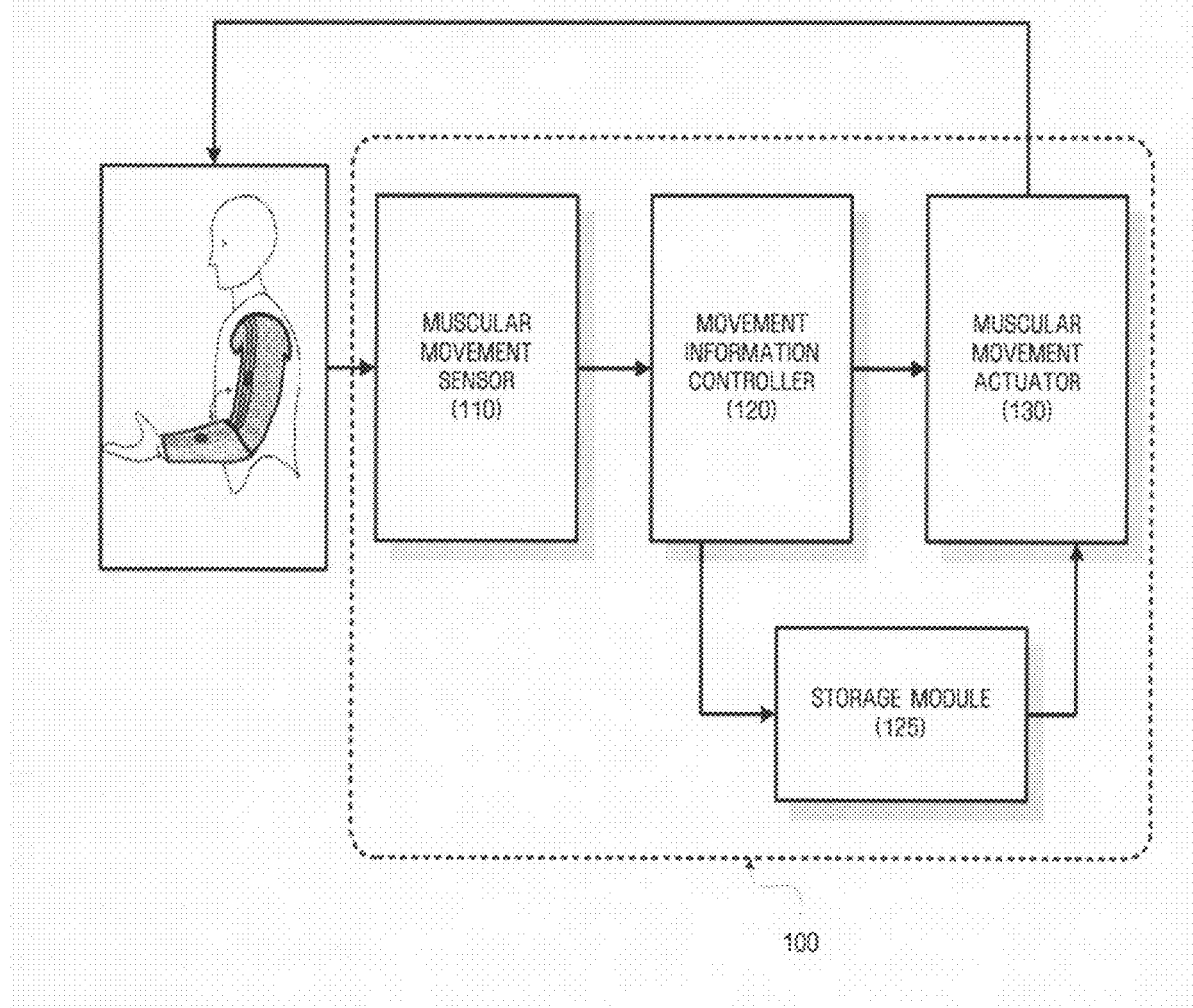
FIG. 2 illustrates an apparatus, such as that illustrated in FIG. 1, according to an embodiment of the present invention.

FIG. 2 illustrates an apparatus 100, such as that illustrated in FIG. 1. Referring to FIG. 2, the apparatus 100 may include a muscular movement sensor 110, a movement information controller 120, a storage module 125, and a muscular movement actuator 130, for example.

When a user wears the apparatus 100 and causes to move a muscle that is, e.g., fully surrounded by the apparatus 100, the muscular movement sensor 110 may detect the movement of the muscle. A sensor using optical fibers or a bioelectric sensor may be used as the muscular movement sensor 110. Some sensing methods used by the muscular movement sensor 110 may be well known to one of ordinary skill in the art to which the present invention pertains, and thus, a detailed description thereof will be omitted.

The movement information controller 120 may analyze the muscular movement, sensed by the muscular movement sensor 110, and generate muscular movement information based on the results of the analysis, for example to control movement of the muscle. The muscular movement information may include the strength and direction of the muscular movement sensed by the muscular movement sensor 110.

The storage module 125 may store muscular movement information in a database according to a set of standards, for example. The movement information controller 120 may then control the muscular movement actuator 130 with reference to the muscular movement information stored in the storage module 125.

In an embodiment, the movement information controller 120 may supply the muscular movement actuator 130 with an input voltage having an appropriate waveform with reference to the storage module 125. Examples of the input voltage include, without limitation, voltages having various waveforms such as direct current (DC) voltages and alternating current (AC) voltages having a sinusoidal wave, a triangle wave, or a square wave.

The muscular movement actuator 130 may be supplied with the input voltage, and may enhance the muscular movement of the user according to the muscular movement information provided by the movement information controller 120, or the muscular movement information stored in the storage module 125, for example. The muscular movement actuator 130 may thus enhance the muscular movement of the user, thereby not only providing additional strength, but also potentially weakening or decreasing the muscular movement of the user, by selectively resisting the movement of the user, for example.

The storage module 125 may store muscular movement information such as the strength and direction of the muscular movement of the user by mapping the muscular movement information as a database according to a set of standards, for example, according to the gender and age of the user, part of the user's body surrounded by the apparatus 100, and corresponding muscles, and the time when the user may use the apparatus 100. The muscular movement information stored in the storage module 125 may further be updated for each of the standards. Then, when the user uses his/her muscles more intensely than he/she usually does, the muscular movement actuator 130 may reduce the strength of the muscular movement of the user according to the muscular movement information stored in the storage module 125, for example. In addition, if a muscle movement exceeds a desired range because of weakness in a muscle, such as a weak bicep muscle, further potentially resulting in the dropping of a held item, an opposing movement force may be generated to maintain the normal holding position.

As an example of increasing the strength, it may be assumed that a muscular strength of one hundred, on a hypothetical scale, is needed to lift a predetermined object. A user who can exert a muscular strength of up to eighty, on the hypothetical scale, can lift the predetermined object by making up for a deficit in muscular strength of twenty with the aid of the apparatus 100. A user who can exert a muscular strength of up to ninety, on a hypothetical scale, can also lift the predetermined object by referencing the muscular movement information stored in the storage module 125 and making up for a deficit in muscular strength of ten, on a hypothetical scale, with the aid of the apparatus 100.

The structure of the muscular movement actuator 130 will hereinafter be described in detail. The muscular movement actuator 130 may include an EAP that can be configured as fiber, e.g., tissue resembling human muscle tissue, and include a pair of electrodes that contact the lateral sides of the EAP, although other quantities of electrodes may be used, and an electric circuit that applies a voltage to the electrodes. The muscular movement actuator 130 may generate additional muscular strength or displacement for the user by responding to a signal obtained through conversion by the movement information controller 120, and an actuator interface (not shown).

The actuator interface (not shown) may be arbitrarily connected between the muscular movement actuator 130 and the movement information controller 120, and may convert a signal generated by the movement information controller 120 into an appropriate signal for driving the muscular movement actuator 130, for example. Examples of the actuator interface may include a power amplifier, a switch, a digital-to-analog (DAC) converter, an analog-to-digital converter (ADC), and other components.

Two types of EAPs and the physical characteristics of each of the two types of EAPs will hereinafter be described in detail with reference to FIG. 3, noting that alternatives are equally available.

EAPs are polymers that are manufactured and processed to reflect a wide range of physical and electrical properties. When EAPs are activated by applying a voltage, they display a significant size or shape distortion or deformation. The degree of deformation of EAPs is dependent on the length, width, thickness, and radial direction of the material of each EAP. In general, EAPs are deformed by 10-50% when activated. Given that piezoelectric materials are generally deformed by less than 0.3%, the degree of deformation of EAPs is highly distinctive. EAPs can also be precisely controlled using an appropriate electric system.

EAPs are generally small, easy to control, consume small amounts of power, achieve high response speeds, and are inexpensive. EAPs are thus, hereby suggested to be widely employed in the field of artificial muscles, and research on potential applications of EAPs as artificial muscles has been vigorously conducted.

EAPs output an electric signal when they undergo physical deformation due to external forces. Thus, EAPs can be used as sensors. Since most EAP materials generate an electrically measurable electrical potential difference, EAPs can also be used as strength, location, velocity, acceleration, and pressure sensors. Further, since most EAPs have bidirectional properties, EAPs can be used as sensors or actuators.

Examples of EAPs may include EAP gels, ionic polymer metal composites (IPMC), and electrostrictive polymers. The operating principles of most EAP materials are based on ionic movements inside and outside a polymer network.

EAPs are broadly classified into dry polymers using a dielectric material and wet polymers using an ionic material. The upper view and the lower view of FIG. 3 respectively illustrate a dry polymer and a wet polymer.

Figure 3:
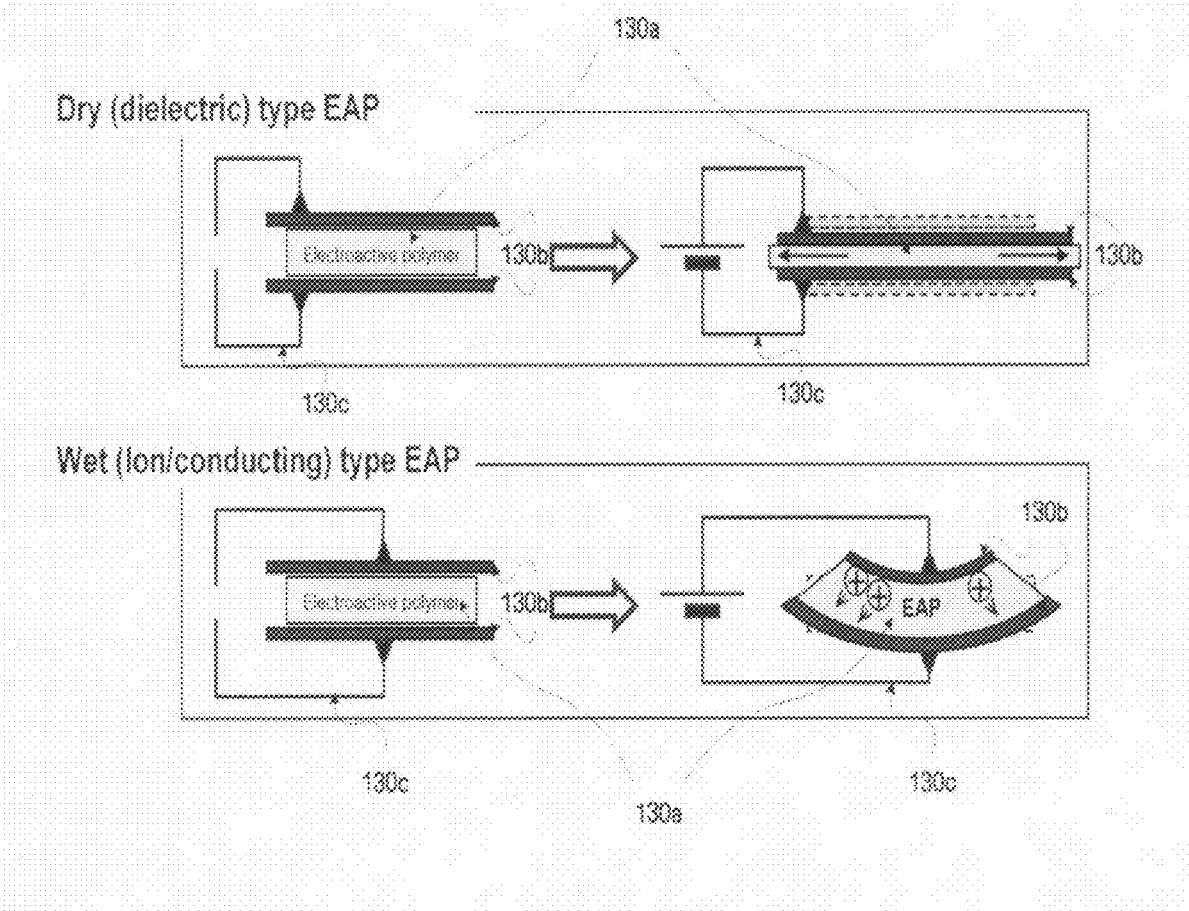
FIG. 3 illustrates two types of electroactive polymers (EAPs) and the characteristics of each of the two types of EAPs, according to an embodiment of the present invention.

Referring to the upper and lower views of FIG. 3, each of the dry and wet polymers may be formed as a sandwich made up of a dielectric or ionic polymer 130a and two conductive/compliant electrodes 130b that are on the opposite sides of the dielectric or ionic polymer 130a. When a high electric field (e.g., an electric field of several hundreds or thousands of volts) generated by an electric circuit 130c is applied, the suction force of the electrodes 130b increases and thus presses on the dielectric or ionic polymer 130a that is interposed between the electrodes 130b, thereby causing a significant deformation of the dielectric or ionic EAP 130a so that the dry or wet polymer can elongate or bend in one direction. Here, the degree of deformation of the dry or wet polymer may be about 50%.

Referring to the upper view of FIG. 3, two electrodes 130b contact an EAP 130a, having a predetermined thickness, on the opposite sides of the EAP 130a, for example. Each of the electrodes 130b is formed of a conductive polymer layer. In order for the electrodes 130b to be deformed along with the EAP 130a, the electrodes 130b should be compliant as well as conductive. An initial state of the EAP 130a when the electrodes 130b are not supplied with power by an electric circuit 130c is illustrated in the left part of the upper view of FIG. 3. Once the electrodes 130b are supplied with power by the electric circuit 130c, the thickness of the EAP 130a decreases, and thus, the EAP 130a spreads wide between the electrodes 130b, as illustrated in the right part of the upper view of FIG. 3. Here, the electrodes 130b that are compliant are deformed along with the EAP 130a.

Referring to the lower view of FIG. 3, two electrodes 130b contact an EAP 130a, having a predetermined thickness, on the opposite sides of the EAP 130a, for example. Each of the electrodes 130b may be formed of a conductive polymer layer. In an embodiment, in order for the electrodes 130b to be deformed along with the EAP 130a, the electrodes 130b should be compliant as well as conductive. An initial state of the EAP 130a when the electrodes 130b are not supplied with power by an electric circuit 130c is illustrated in the left part of the lower view of FIG. 3. Once the electrodes 130b are supplied with power by the electric circuit 130c, ions in the EAP 130a rush into a cathode, thereby causing a deformation of the EAP 130a so that the EAP 130a bends like a bow, as illustrated in the right part of the lower view of FIG. 3. Here, the electrodes 130b that are compliant bend along with the EAP 130a.

Figure 4:
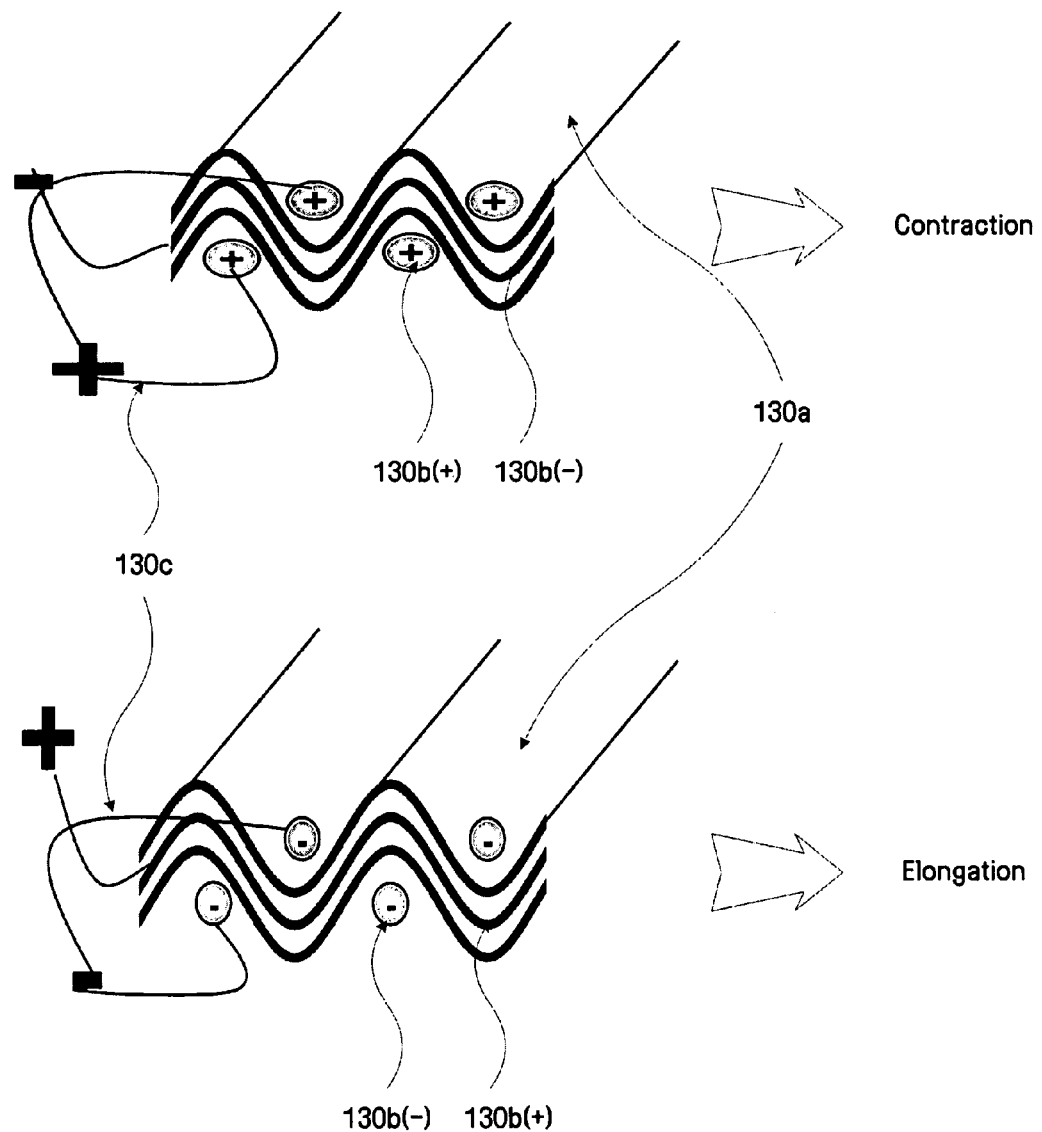
FIG. 4 illustrates an explanation of the principles of realization of a muscular movement actuator, according to an embodiment of the present invention.

The principles of realization of an actuator using the wet polymer illustrated in the lower view of FIG. 3 will hereinafter be described in detail with reference to FIG. 4. Referring to FIG. 4, an EAP 130a having a uniform curvature may be formed as a wave, for example, one of a cathode 130b(−) and an anode 130b(+) may be inserted into curvature portions of the EAP 130a, and an anode 130b(+) or a cathode 130b(−) (whichever of the cathode 130b(−) and the anode 130b(+) connected to none of the curvature portions of the EAP 130a) may be inserted into the middle of the EAP 130a. When the anode 130b(+) and the cathode 130b(−) are supplied with power by an electric circuit 130c, the curvature of the EAP 130a changes in the direction of a current, and thus, the EAP 130a either contracts or elongates.

Examples of the action of a muscular movement actuator using an EAP will hereinafter be described in detail with reference to FIGS. 5 through 7B.

Figure 5:
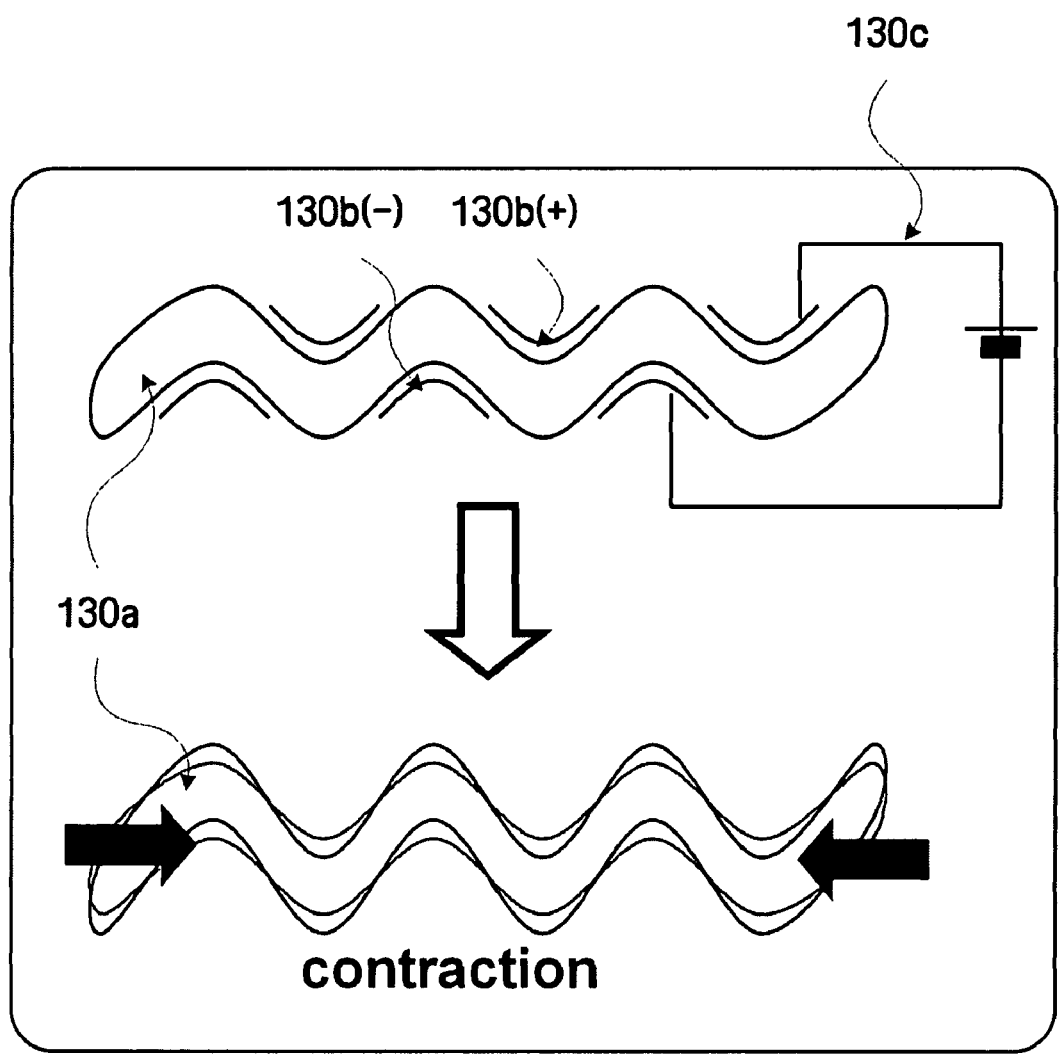
FIG. 5 illustrates an explanation for the action of a muscular movement actuator, according to an embodiment of the present invention.

FIG. 5 illustrates an explanation for the action of a muscular movement actuator according to an embodiment of the present invention. Referring to FIG. 5, an EAP 130a may be formed as a single wavy layer having a uniform curvature, a pair of electrodes 130b may be formed by connecting one of an anode 130b(+) and a cathode 130b(−) to an upper curvature portion of the EAP 130a and connecting whichever of the anode 130(+) and the cathode 130b(−) is left unconnected to the upper curvature portion of the EAP 130a to a lower curvature portion of the EAP 130a. When a current is applied to the electrodes 130b by an electric circuit 130c that is connected to a power supply, the EAP 130a bends in one direction, thereby causing a deformation of the EAP 130a so that the EAP 130a contracts.

Figure 6:
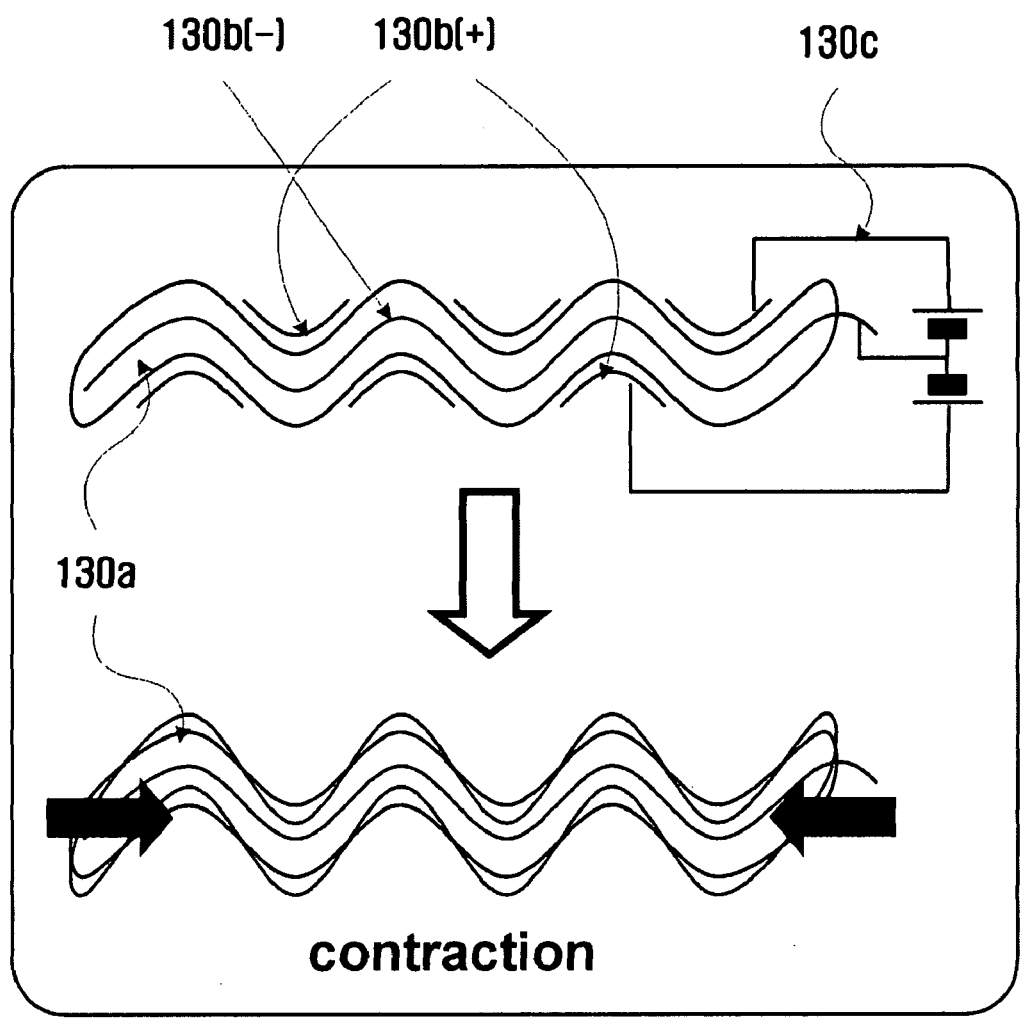
FIG. 6 illustrates an explanation for the action of a muscular movement actuator, according to another embodiment of the present invention.

FIG. 6 illustrates an explanation for the action of a muscular movement actuator according to another embodiment of the present invention. Referring to FIG. 6, an EAP 130a may be formed as a double wavy layer having a uniform curvature. A pair of electrodes 130b may be formed by connecting one of an anode 130b(+) and a cathode 130b(−) to both upper and lower curvature portions of the EAP 130a and connecting whichever of the anode 130b(+) and the cathode 130b(−) is connected to none of the upper and lower curvature portions of the EAP 130a to the interface between the upper layer and the lower layer of the EAP 130a. When a current is applied to the electrodes 130b by an electric circuit 130c that is connected to a power supply, the EAP 130a further bends in one direction so that the EAP 130a further contracts.

Figure 7A:
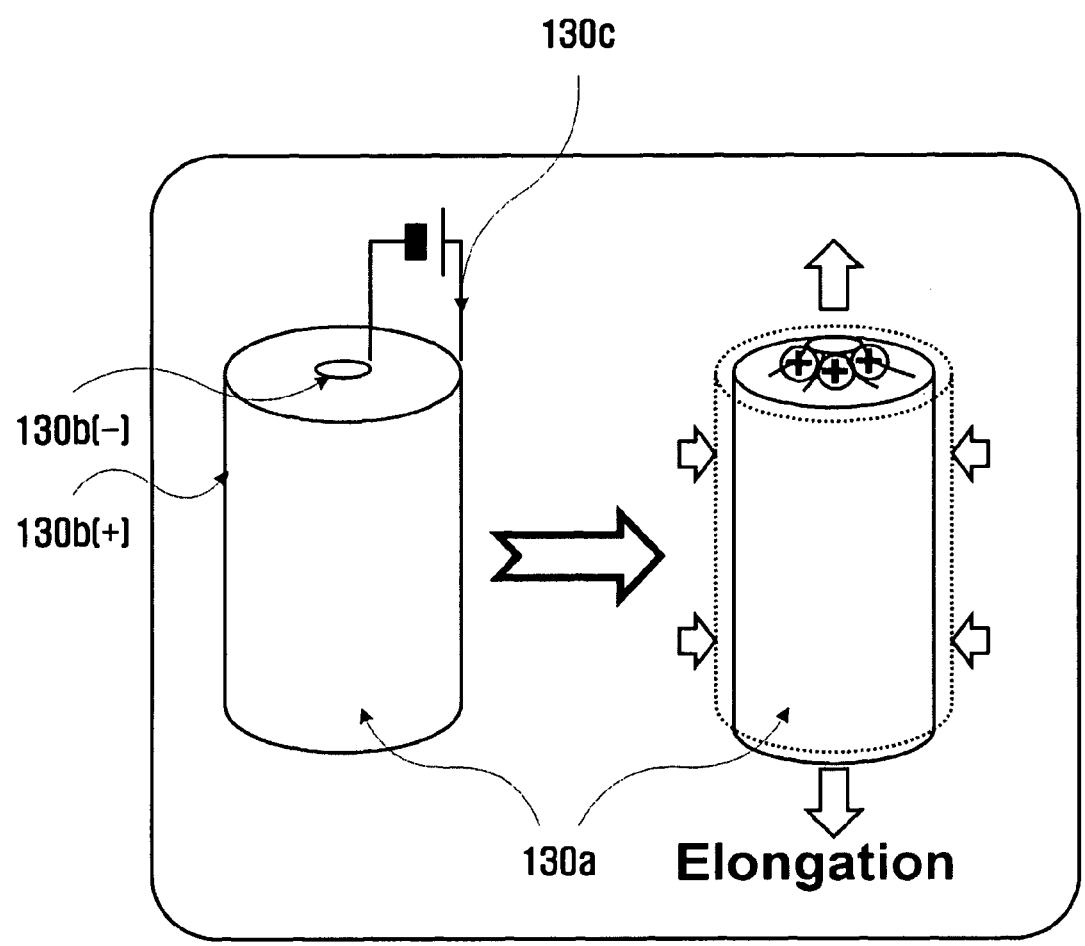
FIGS. 7A and 7B illustrate an explanation for the action of a muscular movement actuator, according to another embodiment of the present invention.
Figure 7B:
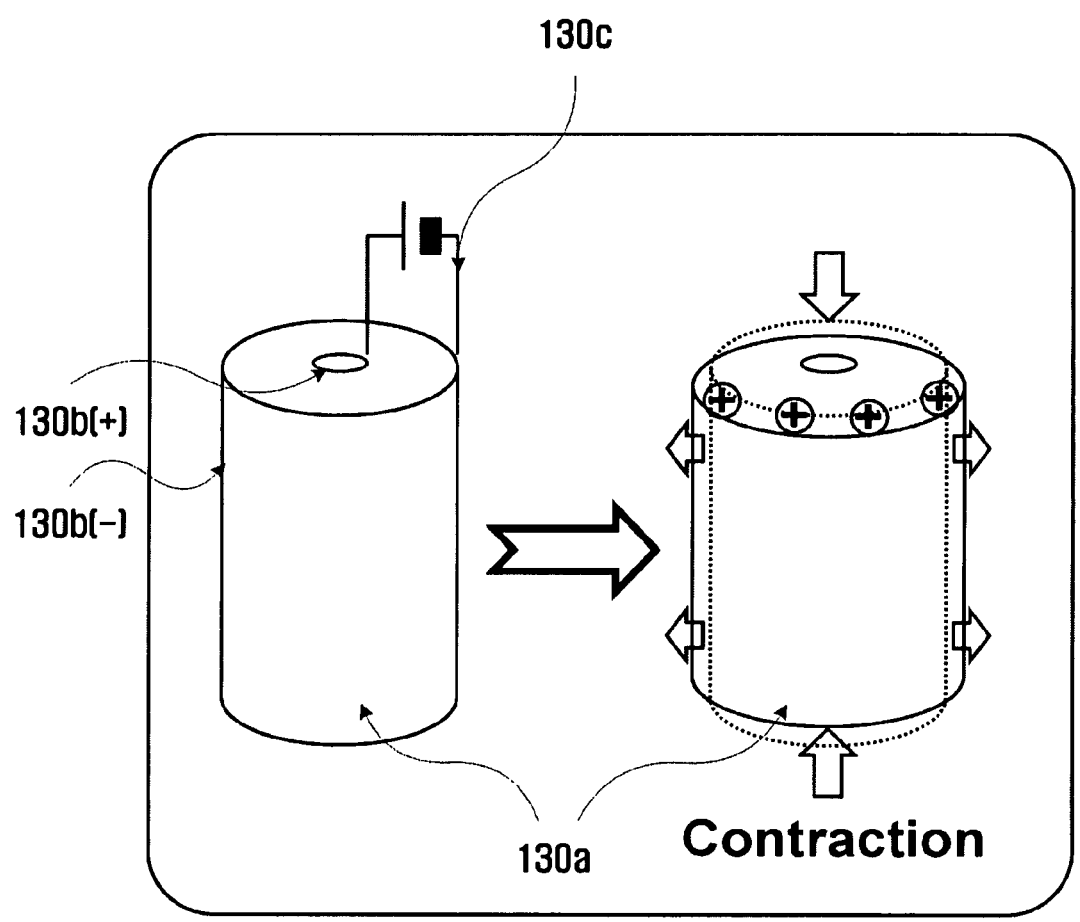

FIGS. 7A and 7B illustrate an explanation for the action of a muscular movement actuator according to another embodiment of the present invention. Referring to FIGS. 7A and 7B, an EAP 130a may be formed as a cylinder that extends longer in a longitudinal direction than in a latitudinal direction. A pair of electrodes 130b may be formed by connecting one of an anode 130b(+) and a cathode 130b(−) to the outer circumferential surface of the EAP 130a and connecting whichever of the anode 130*b*(+) and the cathode 130*b*(−) is left unconnected to the outer circumferential surface of the EAP 130*a* to the inner circumferential surface of the EAP 130*a* which is the outer circumferential surface of a central axial member of the EAP 130*a*, for example.

In detail, Referring to FIG. 7A, the volume of a central portion of the EAP 130*a* varies, and thus, the central axial member of the EAP 130*a* extends. Accordingly, the EAP 130*a* elongates. FIG. 7B illustrates the opposite situation to the situation illustrated in FIG. 7A. In other words, referring to FIG. 7B, the volume of an outer circumferential portion of the EAP 130*a* increases, and thus, the diameter of the EAP 130*a* increases so that the EAP 130*a* contracts along the longitudinal direction.

The apparatus 100 may be realized as outerwear or underwear that can be worn by a user, for example. In this case, it is possible to facilitate user activities by providing a user who wears the apparatus 100 with almost the same feeling of wearing outerwear or underwear. The apparatus 100 may enhance the muscular movement of a user and may serve as auxiliary artificial muscles for a user.

The apparatus for enhancing muscular movement according to the present invention may be realized, using fibers, as clothes that provide almost the same arrangement as that of the human muscles, thereby enhancing muscular movement of individuals, such as elderly people who have weak muscular strength.

In addition, the apparatus for enhancing muscular movement according to the present invention may prevent excessive muscular movement of a user who has weak muscular strength by limiting the movement of the individuals and can correct posture so that a user can properly maintain a desired posture.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A wearable apparatus to enhance a muscular movement, the wearable apparatus comprising:
   at least one muscular movement sensor to sense a result of an initial muscular movement;
   a muscular movement actuator positioned external to a muscle; and
   a movement information controller to analyze the sensed result of the muscular movement and to generate muscular movement information configured to control the muscular movement actuator based on the analyzed muscular movement,
   wherein the muscular movement actuator is adapted to enhance the movement of the muscle, according to the muscular movement information generated by the movement information controller, by actively controlling a deformation of the muscle movement actuator over the surface of the muscle.

2. The apparatus of claim 1, wherein the muscular movement information comprises an intensity and a direction of the movement of the muscle.

3. The apparatus of claim 1, further comprising a storage module to store the muscular movement information as a database according to a set of standards,
   wherein the movement information controller controls the muscular movement actuator according to the muscular movement information stored in the storage module.

4. The apparatus of claim 3, wherein the standards comprise at least one of a gender of a user of the apparatus, an age of a user of the apparatus, a user body part to which the muscle corresponds, and a time when the user uses the apparatus.

5. The apparatus of claim 1, wherein the muscular movement actuator comprises:
   an electroactive polymer (EAP) configured as one of fibers and a pad;
   a pair of electrodes to contact opposite lateral sides of the EAP; and
   an electric circuit to apply a voltage to the electrodes.

6. The apparatus of claim 5, wherein the EAP is a wet polymer that causes movement of ions inside the wet polymer according to the intensity of the voltage, wherein the voltage varies according to the muscular movement information provided by the movement information controller.

7. The apparatus of claim 6, wherein the EAP contracts or relaxes the muscle by increasing or reducing curvature according to a movement of ions.

8. The apparatus of claim 7, wherein the EAP is formed as a single wavy layer having a uniform curvature, and the electrodes are formed by connecting one of an anode and a cathode to an upper curvature portion of the EAP and connecting whichever of the anode and the cathode is left unconnected to the upper curvature portion of the EAP to a lower curvature portion of the EAP.

9. The apparatus of claim 7, wherein the EAP is formed as a double wavy layer having a uniform curvature, and the electrodes are formed by connecting one of one of an anode and a cathode to the upper and lower curvature portions of the EAP and connecting whichever of the anode and the cathode is connected to none of the upper and lower curvature portions of the EAP to an interface between upper and lower parts of the EAP.

10. The apparatus of claim 7, wherein the EAP is formed as a cylinder that extends longer in a longitudinal direction than in a latitudinal direction, and the electrodes are formed by connecting one of an anode and a cathode to an external circumferential surface of the cylinder and connecting whichever of the anode and the cathode is left unconnected to the external circumferential surface of the cylinder to an inner circumferential surface of the cylinder that contacts a central axial member of the cylinder.

11. The apparatus of claim 1, wherein the apparatus is clothing wearable over a surface of the muscle.

12. A wearable apparatus to enhance a muscular movement, the wearable apparatus comprising:
   at least one muscular movement sensor to sense a result of an attempt to move a muscle;
   a movement information controller to analyze the sensed muscular movement attempt, and to generate muscular movement information based on the analyzed muscular movement attempt, wherein the generated muscular movement information includes data configured to control an auxiliary artificial muscle formed of fibers; and
   a muscular movement actuator to enhance the movement of the muscle, according to the muscular movement information generated by the movement information controller, by actively controlling a deformation of the muscle movement actuator over the surface of the muscle.

13. The apparatus of claim 12, wherein the auxiliary artificial muscle is clothing wearable over a surface of the muscle.

14. A wearable apparatus to enhance a muscular movement, the wearable apparatus comprising:

a movement information controller to analyze a muscular movement attempt, and to generate muscular movement information configured to control an electroactive polymer actuator positioned external to the muscle based on the analyzed muscular movement attempt; and a muscular movement actuator including an electroactive polymer to enhance the movement of the muscle according to the generated muscular movement information by actively controlling a deformation of the muscle movement actuator over the surface of the muscle.

\* \* \* \* \*

UNITED STATES PATENT AND TRADEMARK OFFICE
CERTIFICATE OF CORRECTION

| | | |
|---|---|---|
| PATENT NO. | : 7,966,074 B2 | Page 1 of 1 |
| APPLICATION NO. | : 11/797760 | |
| DATED | : June 21, 2011 | |
| INVENTOR(S) | : Kim et al. | |

It is certified that error appears in the above-identified patent and that said Letters Patent is hereby corrected as shown below:

In the Claims

Column 8, Line 30, In Claim 9, delete "one of one of" and insert -- one of --, therefor.

Signed and Sealed this
First Day of July, 2014

Michelle K. Lee
*Deputy Director of the United States Patent and Trademark Office*